United States Patent
Katz

(10) Patent No.: US 10,783,137 B2
(45) Date of Patent: Sep. 22, 2020

(54) IDENTITY MANAGEMENT

(71) Applicant: Experian Health, Inc., Franklin, TN (US)

(72) Inventor: Elazar Katz, Boynton Beach, FL (US)

(73) Assignee: EXPERIAN HEALTH, INC., Franklin, TN (US)

( * ) Notice: Subject to any disclaimer, the term of this patent is extended or adjusted under 35 U.S.C. 154(b) by 306 days.

(21) Appl. No.: 15/456,053

(22) Filed: Mar. 10, 2017

(65) Prior Publication Data
US 2018/0260432 A1    Sep. 13, 2018

(51) Int. Cl.
| | |
|---|---|
| G06F 16/23 | (2019.01) |
| G16H 10/60 | (2018.01) |
| G16H 40/20 | (2018.01) |
| G16H 50/70 | (2018.01) |
| H04L 9/32  | (2006.01) |

(52) U.S. Cl.
CPC ......... *G06F 16/2365* (2019.01); *G16H 10/60* (2018.01); *G16H 40/20* (2018.01); *G16H 50/70* (2018.01); *H04L 9/3239* (2013.01); *H04L 2209/046* (2013.01)

(58) Field of Classification Search
CPC .... G06F 16/2365; G06F 16/532; G06F 16/28; G06F 16/288
See application file for complete search history.

(56) References Cited

U.S. PATENT DOCUMENTS

| | | | | |
|---|---|---|---|---|
| 7,720,846 | B1* | 5/2010 | Bayliss | G06F 16/285 |
| | | | | 707/736 |
| 8,495,384 | B1* | 7/2013 | DeLuccia | G06F 16/215 |
| | | | | 713/189 |
| 8,965,848 | B2* | 2/2015 | Caceres | G06F 16/215 |
| | | | | 707/626 |
| 9,785,696 | B1* | 10/2017 | Yakhnenko | G06F 16/285 |
| 9,864,746 | B2* | 1/2018 | Gilder | G06F 16/93 |
| 2005/0147947 | A1* | 7/2005 | Cookson, Jr. | G06F 16/20 |
| | | | | 707/E17.012 |
| 2011/0179011 | A1* | 7/2011 | Cardno | G06F 16/90 |
| | | | | 707/709 |
| 2014/0372458 | A1* | 12/2014 | Jurca | G06F 16/9024 |
| | | | | 707/754 |
| 2016/0283548 | A1* | 9/2016 | Han | G06F 16/9535 |
| 2016/0335341 | A1* | 11/2016 | Krauss | G06F 16/367 |

* cited by examiner

*Primary Examiner* — Ashish Thomas
*Assistant Examiner* — Jedidiah P Ferrer
(74) *Attorney, Agent, or Firm* — Merchant & Gould

(57) ABSTRACT

An identity management method includes comparing person-to-person relationship data of at least two identifiers of individuals to determine if the at least two identifiers have a relationship with a common third party identifier. The person-to-person relationship data is obtained from one or more sources and the at least two identifiers are the same or similar. When it is determined that the at least two identifiers have a relationship with a common third party identifier, the method further includes generating an output indicating that the at least two identifiers actually identify the same individual. The output can alternatively, or further, include a confidence level indicative of the confidence that the at least two identities do indeed identify the same individual. The person-to-person relationship analysis can be combined with other forms of identity matching, e.g., demographics.

20 Claims, 6 Drawing Sheets

Employee Record 200

| Field | Ref |
|---|---|
| Employee Number | 210a |
| First Name | 210b |
| Middle Name / Initial | 210c |
| Last Name | 210d |
| Home Address | 210e |
| Home Phone | 210f |
| Cell Phone | 210g |
| E-mail Address | 210h |
| Date of Birth | 210i |
| Gender | 210j |
| Social Security Number | 210k |
| Names of Schools Attended | 210l |
| Employer Name | 210m |
| Employer Address | 210n |
| Work Phone | 210o |

FIG. 2A

Insurance Claim Form 200

| Field | Ref |
|---|---|
| Insurance I.D. Number | 220a |
| First Name | 220b |
| Middle Name / Initial | 220c |
| Last Name | 220d |
| Home Address | 220e |
| Home Phone | 220f |
| Cell Phone | 220g |
| E-mail Address | 220h |
| Former Last Name | 220i |
| Former Address | 220j |
| Employer Name | 220k |
| Employer Address | 220l |
| Work Phone | 220m |
| Date of Birth | 220n |
| Social Security Number | 220o |
| Gender | 220p |
| Medical Provider Name | 220q |
| Medical Provider ID | 220r |
| Insurance Company | 220s |
| Insurance Holder | 220t |
| Responsible Party | 220u |
| Address Respons. Party | 220v |
| Name of Dependents | 220w |
| Date of Birth/Gender of Dependents | 220x |

FIG. 2B

Birth Certificate/School Enrollment 200

| Field | Ref |
|---|---|
| First Name | 230a |
| Middle Name / Initial | 230b |
| Last Name | 230c |
| Gender | 230d |
| Date of Birth | 230e |
| Location of Birth | 230f |
| Mother First Name | 230g |
| Mother Middle Name/Init | 230h |
| Mother Last Name | 230i |
| Father First Name | 230j |
| Father Middle Name/Init | 230k |
| Father Last Name | 230l |
| Home Address | 240a |
| Home Phone | 240b |
| Student I.D. | 240c |

FIG. 2C

| Document | Person-to-Person Relationship Established by Document Data |
|---|---|
| Medical Ins. Claim Form | Patient-to-Doctor; Child Patient-to-Parent/Guardian; Patient-to-Responsible Party |
| Birth Certificate | Child-to-Mother; Child-to-Father |
| School Enrollment | Child-to-Mother/Guardian; Child-to-Father/Gardian; Child-to-Emergency Contact |
| Will | Testator-to-Executor; Testator-to-Beneficiary; Executor-to-Beneficiary |
| Trust | Grantor-to-Trustee; Grantor-to-Beneficiary; Trustee-to-Beneficiary |
| Power of Attorney | Principal-to-Attorney in Fact |
| Tax Filings | Filer-to-Co-Filer; Filer-to-Dependents |
| Life Insurance Policy | Policy Holder-to-Insured; Policy Holder-to-Beneficiary; Insured-to-Beneficiary |
| Bank Account Statement | Account Owner-to-Joint Account Owner; Account Owner-to-Named Third Party |
| Deed | Transferor-to-Transferee |
| Child Summer Camp Registration | Child-to-Parent; Child-to-Emergency Contact; Child-to-Pediatrician; Child-to-Dentist |

FIG. 3

IDENTITY MANAGEMENT

BACKGROUND

Individuals interact with numerous entities, e.g., local, state and federal governments, utility companies, health care providers, insurance companies, banking institutions, employers, educational institutions, retailers, etc. Each of these entities often keep one or more of their own records in relation to the individual by assigning the individual an identifier, e.g., identification (I.D.) number or code, and storing all other information relevant to the individual and their interactions with the entity under that identifier. For example, each entity might keep a record for an individual under an assigned I.D. code that includes the individual's demographic information such as name, home address, telephone number(s), e-mail address(es), as well as transactional data identifying transactions between the individual and the entity, e.g., payments by or to the individual, services provided by or to the individual, items purchased by the individual, etc. As such, each individual likely has tens, if not hundreds, of records existing in the digital world that identify that individual with at least demographic information and possibly with a history of entity interactions.

Consequently, it is very possible to come across two or more of the same or similar identifiers, e.g., Jon Smith, Jonathan Smith and Jon Q. Smith, yet be uncertain as to whether the same or similar identifiers actually identify the same individual or different individuals. Currently, identification systems use cross-correlation between names and demographic information from various sources to determine if identifiers identify the same person or identify distinct individuals. However, there are other types of information available, e.g. relationship data, which demographic identification systems fail to utilize.

BRIEF SUMMARY

The present disclosure is directed to systems and methods for correlating person-to-person relationship data across sources to determine if a plurality of same or similar identifiers identify the same individual or different individuals. The use of person-to-person relationship data analysis can be used alone or in conjunction with demographic information data analysis to correlate information related to same or similar identifiers.

More specifically, the identity management system and method of the present disclosure operate to find correlations or commonalities (e.g., exact matches, partial matches, shared attributes, shared features, etc.) in person-to-person relationship data, which are obtained from one or more data sources. The correlations from the person-to-person relationship data are used by the identity management system and method to determine whether two or more identifiers, which are the same or are similar (e.g. resembling another identifier without being identical), likely identify the same individual based on the existence of one or more common relationships, or links, between the same (or similar) identifiers and a third party identifier.

The same or similar identifiers, as well as the third party identifiers, can be provided in various forms such as an alphanumeric identifier (e.g., identification number, first name, last name, middle name, address, gender, telephone number, e-mail address, etc.), a graphical identifier, and/or an encrypted identifier (e.g., a cryptographic hash).

In certain embodiments, the identity management system and method produce a binary output (e.g., yes/no), that the same or similar identifiers identify the same individual (yes) or do not identify the same individual (no). In certain embodiments, additionally or alternatively, the identity management system and method produce an output representative of a confidence level that the same or similar identifiers identify the same individual. The confidence level is based on the existence of one or more common relationships between the same (or similar) identifiers and a third party identifier. The higher number of common relationships between the same (or similar) identifiers and a third party identifiers, the higher the confidence level.

In certain embodiments, the identity management system and method can also utilize demographic data in combination with the person-to-person relationship data to correlate identifiers. In certain embodiments, the identity management system and method operate on person-to-person relationship data (and/or demographic data) that is obfuscated, for example, by cryptographic data hashing. In certain embodiments, the identity management system and method produce one or more outputs that are obfuscated, for example, by cryptographic data hashing.

BRIEF DESCRIPTION OF THE DRAWINGS

The accompanying drawings, which are incorporated in and constitute a part of this disclosure, illustrate various aspects and examples of the present invention. In the drawings:

FIGS. 2A-2C provide example listings of identity data that can be utilized by an identity management system or method.

FIG. 3 provides an example listing of the various types of relationship data that can be obtained from commonly used forms or documents.

DETAILED DESCRIPTION

Figure 1:
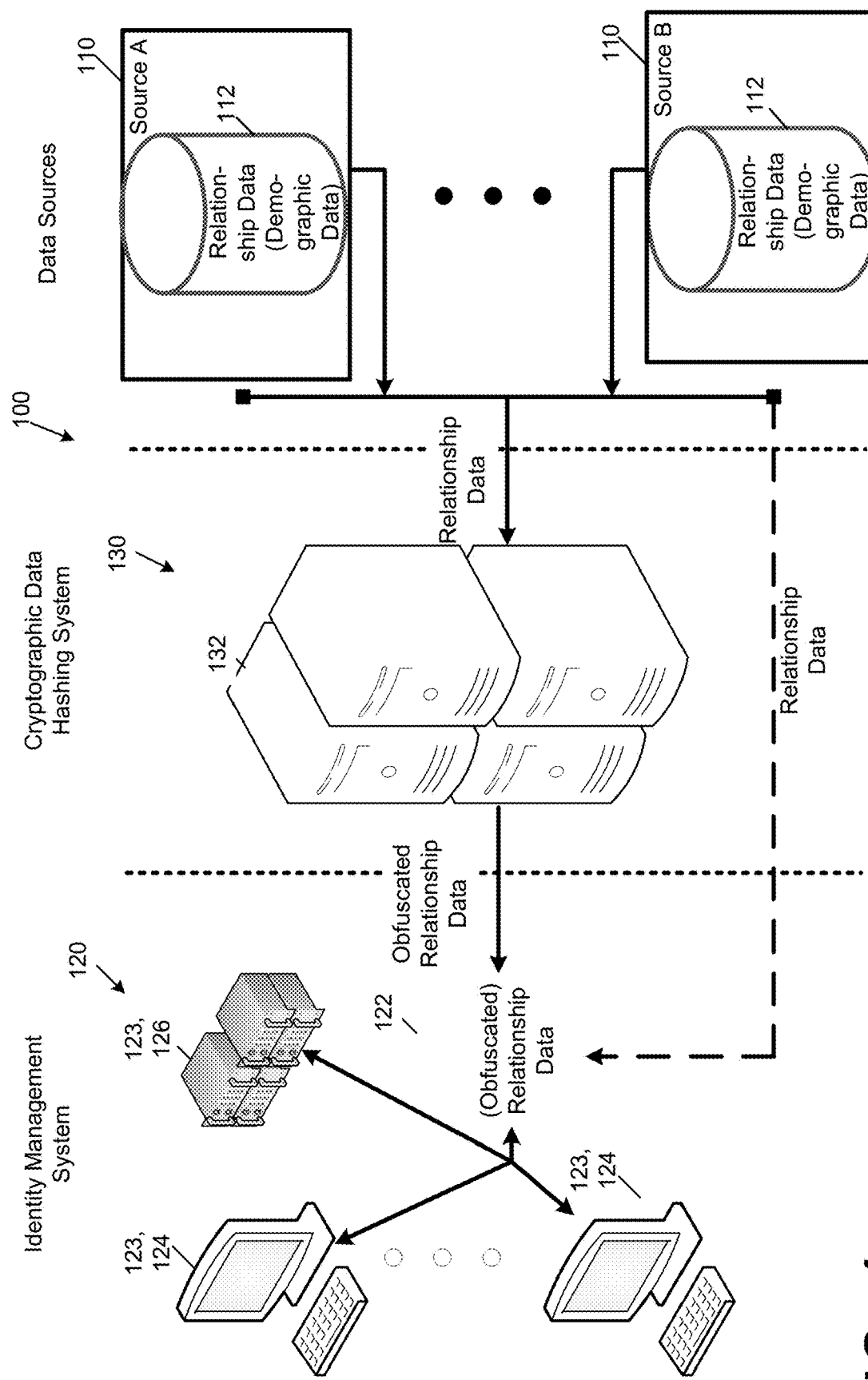
FIG. 1 is a schematic illustrating an example environment in which identity management can be implemented.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications can be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not be taken in a limiting sense.

The present disclosure is directed to an identity management system and method. The identity management system and method operate to find correlations, commonalities (e.g., exact matches, partial matches, shared attributes, shared features, etc.), or links in person-to-person relationship data, which are obtained from one or more data sources. The correlations from the person-to-person relationship data are then used by the identity management system and method to determine whether two or more of the same or similar identifiers, such as an alphanumeric identifier (e.g., identification number, first name, last name, middle name, address, gender, telephone number, e-mail address, cryptographic hash, etc.), a graphical identifier and/or encrypted identifier, likely identify the same individual or different individuals. In certain embodiments, the identity management system and method produces a binary output (e.g., yes/no), that the same or similar identifiers identify the same individual (yes) or do not identify the same individual (no). In certain embodiments, additionally or alternatively, the identity management system and method produce an output indicating a confidence level as two whether the same or similar identifiers identify the same individual (e.g., two same or similar identifiers are shown as having common links to three or four third party identifiers indicating a high confidence level that the two same or similar identifiers are identifying the same individual). In certain embodiments, the identity management system and method can also utilize demographic data in combination with the person-to-person relationship data to correlate identifiers. In certain embodiments, the identity management system and method perform a commonality analysis on person-to-person relationship data that is obfuscated, for example, by cryptographic data hashing.

FIG. 1 is a schematic illustrating an example environment 100 in which systems and methods for identity management can be implemented. In the example environment, a plurality of sources 110 (e.g., utility companies, health care providers, insurance companies, banking institutions, employers, educational institutions, retailers, government offices, etc.) maintain records on individuals in one or more repositories 112 (e.g., databases). The repositories 112 include at least person-to-person relationship data, and can additionally include demographic data, on a plurality of individuals; the data within the repositories can be entered into the repositories through any type of data entry, e.g., keyboard, scanner, data recorder, etc. The person-to-person relationship data, and, if utilized, demographic data, can be transmitted via wired or wireless communication directly to an identity management system 120. The identity management system 120 includes one or more repositories 122 for storing the received relationship data (and demographic data), which can then be accessed by one or more computing devices 123, e.g., workstations 124, servers 126 or other computing devices such as desktop computers, laptop computers, tablets, smart phones, and the like, for data analysis. The components of computing devices are discussed in greater detail in regard to FIG. 6. Alternatively, or in addition to providing the relationship data directly to the identity management system 120, the relationship data can be obfuscated if there is a desire or a legal mandate to maintain privacy around an individual. In the environment 100 of FIG. 1, a cryptographic data hashing system 130 obfuscates the relationship data. The cryptographic data hashing system 130 can include one or more computing devices 132 (e.g., servers) to execute a cryptographic hash function.

FIGS. 2A-2C provide examples of various types of identity data 200 (e.g., person-to-person relationship data and/or demographic data) that might be provided by different data sources. FIG. 2A provides an example wherein the source comprises an employer and the data listing comprises an employee record having identity data, e.g., identifiers 200, in the form of demographic information about an individual employee including, but not limited to: (a) an employer assigned employee number 210a; (b) the employee's first name 210b; (c) middle name (or middle initial) 210c; (d) last name 210d; (e) home address 210e; (f) home phone number 210f; (g) cell phone number 210g; (h) e-mail address 210h; (i) date of birth 210i; (j) gender 210j; (k) social security number 210k; (I) name of schools attended 210l; (m) employer name 210m; (n) employer address 210n; and (o) employer/work phone number 210o. Different and/or additional identifiers related to the employee can also be available.

FIG. 2B provides an example of identity data, e.g., identifiers 200, wherein the source comprises a healthcare provider and the identifiers comprise information submitted on an insurance claim form that includes data in the form of both demographic information and person-to-person relationship information of an individual patient including, but not limited to: (a) the patient's insurance I.D. number 220a; (b) the patient's first name 220b; (c) the patient's middle name (or middle initial) 220c; (d) the patient's last name 220d; (e) the patient's home address 220e; (f) the patient's home phone number 220f; (g) the patient's cell phone number 220g; (h) the patient's e-mail address 220h; (i) the patient's former last name 220i; (j) the patient's former home address 220j; (k) the patient's employer's name 220k; (l) the patient's employer's address 220l; (m) the patient's work phone number 220m; (n) the patient's date of birth 220n; (o) the patient's social security number 220o; (p) the patient's gender 220p; (q) the name of the patient's medical provider 220q; (r) the medical provider's I.D. 220r; (s) the name of the patient's insurance company 220s; (t) the name of the holder of the insurance (which may or may not be the patient) 220t; (u) the party responsible for payment of the medical provider bill (which may or may not be the patient) 220u; (v) address of the responsible party 220v; (w) names of dependents (e.g., those covered by the named insurance company) 220w; and (x) date of birth and gender of dependents 220x. Notably, the data and identifiers of FIG. 2B provide a person-to-person relationship between the patient and the medical provider, between the patient and the responsible party as well as between the patient and one or more dependents. Different and/or additional data fields or identifiers related to the patient can also be available.

FIG. 2C provides an example of identity data, e.g., identifiers 200, wherein the source comprises a hospital or governmental entity and the data listing comprises information submitted via a birth certificate that includes data in the form of both demographic information and person-to-person relationship information of an individual including, but not limited to: (a) an individual's first name 230a; (b) an individual's middle name (or middle initial) 230b; (c) an individual's last name 230c; (d) an individual's gender 230d; (e) an individual's date of birth 230e; (f) an individual's location of birth 230f; (g) the first name of an individual's mother 230g; (h) the middle name (or middle initial) of an individual's mother 230h; (i) the last name of an individual's mother 230i; (j) the first name of an individual's father 230j; (k) the middle name (or middle initial) of an individual's father 230k; and (l) the last name of an individual's father 230l.

One might find similar information in, for example, school enrollment data provided by an educational institution, which might also provide: (a) an individual's home address 240a; (b) an individual's home phone number 240b;

and (c) an individual's student I.D.; 240c. Notably, the data and identifiers of FIG. 2C provide a person-to-person relationship between the individual and the individual's mother as well as a person-to-person relationship between the individual and the individual's father. Different and/or additional data fields or identifiers related to the individual can also be available.

FIGS. 2A-2C illustrate just a few examples of identity data sources from which identity data can be drawn. FIGS. 2B-2C illustrate that identity data need not only be limited to demographic information but can include person-to-person relationship information from any source that stores and/or tracks such information. For example, person-to-person relationship data can be obtained from any variety of sources such as governmental entities, law firms, life insurance companies, banking institutions, or even a child's summer camp as each of these sources store and/or track documents such as wills, trusts, powers of attorney, tax documents, life insurance policies, bank account statements, property deeds, and summer camp registration forms.

FIG. 3 is a table 300 that illustrates just some of the many common forms/documents and the person-to-person relationship data that can be extracted therefrom. These forms/documents and the person-to-person relationship data established through them include: (a) a Medical Insurance Claim form 310a and Patient-to-Doctor; Child Patient-to-Parent/Guardian; Patient-to-Responsible Party relationships 310b; (b) Birth Certificate 312a and Child-to-Mother; Child-to-Father relationships 312b; (c) School Enrollment 314a and Child-to-Mother/Guardian; Child-to-Father/Guardian; Child-to-Emergency Contact relationships 314b; (d) Will 316a and Testator-to-Executor; Testator-to-Beneficiary; Executor-to-Beneficiary relationships 316b; (e) Trust 318a and Grantor-to-Trustee; Grantor-to-Beneficiary; Trustee-to-Beneficiary relationships 318b; (f) Power of Attorney 320a and Principal-to-Attorney in Fact relationships 320b; (g) Tax Filings 322a and Filer-to-Co-Filer; Filer-to-Dependents relationships 322b; (h) Life Insurance Policy 324a and Policy Holder-to-Insured; Policy Holder-to-Beneficiary; Insured-to-Beneficiary relationships 324b; (i) Bank Account Statement 326a and Account Owner-to-Joint Account Owner; Account Owner-to-Named Third Party relationships 326b; (j) Deed 328a and Transferor-to-Transferee relationships 328b; and (i) Child Summer Camp Registration 330a and Child-to-Parent; Child-to-Emergency Contact; Child-to-Pediatrician; Child-to-Dentist relationships 330b.

In more general terms the relationships between individuals and others can be categorized as third party relationships that include: family relationships, patient-doctor relationships, representative (e.g., legal) relationships, and relationships that fail to fall within the first three categories. The relationship can be illustrated by the linking of an individuals' identifier and the third party's identifier. The person-to-person relationship data provides data for correlation, which up until now has been ignored by identification systems. The flowchart of FIG. 4 illustrates an identity management method 400, executed by the identity management system 120 (see FIG. 1), that can determine whether same or similar identifiers represent the same individual through the use of person-to-person relationship data (e.g., third party identifier links); the use of the relationship data can be alone or in combination with demographic data or other forms of identity matching.

Figure 4:
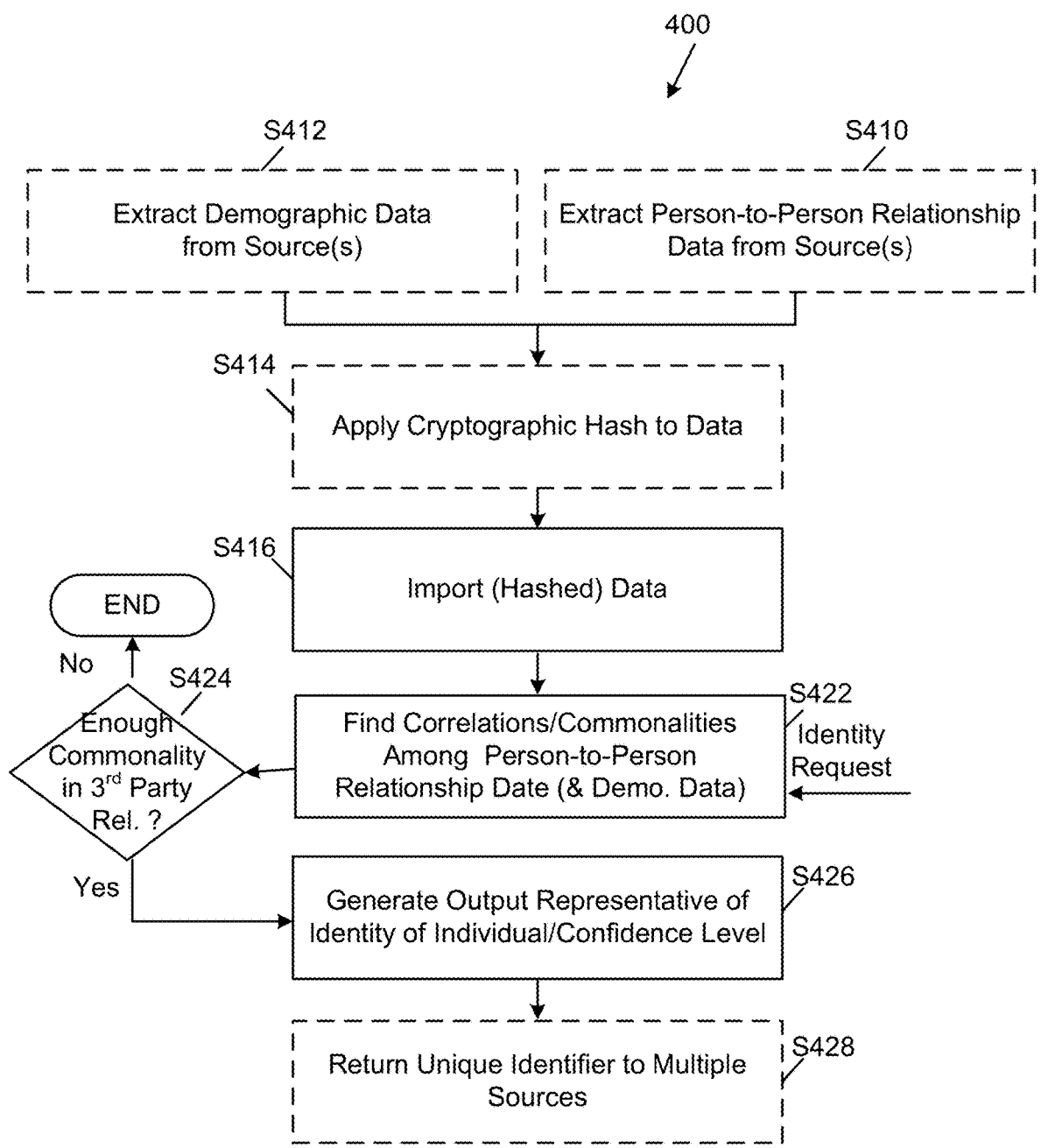
FIG. 4 is a flowchart illustrating an example process for identity management using person-to-person relationship data.

As shown in FIG. 4, the identity management process 400 starts with the extraction of data from one or more sources; the extraction of data includes the extraction of person-to-person relationship data, S410 and can additionally include the extraction of demographic data from one or more sources (some, all or none of which may be the same as the relationship data sources), S412. As indicated by dashed lines, the extraction operations of S410 and S412 can be performed by the identity management system 120 (see FIG. 1) or may be performed by a data mining system external to the identity management system 120. The extracted data can be cryptographically hashed, S414 (if desired) by the identity management system 120 itself or by an obfuscating system, e.g. the cryptographic hashing system 130 of FIG. 1, external to the identity management system 120.

Returning to FIG. 4, the relationship data (and, if utilized, demographic data), in hashed or un-hashed format, are then imported into the one or more repositories 122 of the identity management system 120, S416. The identity management system 120 then operates on the imported data to find correlations or commonalities (e.g., exact matches, partial matches, shared features, shared attributes, etc.) among the relationship data obtained from the different data sources, S422. More specifically, the identity management system 120 operates to determine if two or more of the same or similar identifiers have common links to third party identifiers, e.g., is there a person-to-person relationship between the same or similarly identified individuals and a third party, such as a relative, a doctor, a dentist, a lawyer, etc. If so, there is a likelihood that the same or similar identities are for the same individual; the more common links between the two or more same or similar identifiers and the third party identifiers indicating a higher likelihood that the two or more same or similar identifiers are for the same individual.

Consider the example of two similarly identified individuals, e.g., individuals having identifiers "Jon Smith" and "Jonathan Smith". The identity management system 120 can look at person-to-person relationship data for each identifier and see that both identifiers have common links to children with the same or similar names (e.g., each identifier has a common link to the same third party identifier—the child's name). Such a finding indicates that the two similarly identified individuals are likely the same person. In another scenario, the identity management system 120 can look at person-to-person relationship data for each identifier and see that both identifiers are related to the same doctors (e.g., each identifier has a common link to the same third party identifier—the doctor's name or the doctors I.D. number). Once again, such a finding indicates that the two similarly identified individuals are likely the same person. A finding that each of the identifiers has a common link to both the same child and the same doctor provides a higher confidence level that both of the same or similar identifiers are identifying the same, single individual. If the confidence level is low, or merely if desired, demographic analysis for further confidence in identification can also be performed.

In certain embodiments, person-to-person relationship data analysis is performed prior to, subsequently to, or simultaneously with demographic data analysis. In certain embodiments, relationship data analysis is prompted by user input via a user-interface device, through an "identity request" wherein the user enters some form of identity data, e.g. identifiers such as name(s), I.D.(s), etc. that are the same or similar, to prompt a person-to-person relationship data analysis. In other embodiments, relationship data analysis is performed automatically via a program app and does not require user input.

Continuing with FIG. 4, if the person-to-person relationship data analysis does not yield a sufficient number of third party relationship commonalities to indicate a single individual or provide a desired confidence level, S424:NO, the process 400 is ended or a new round of analysis can begin. However, if the person-to-person relationship data analysis yields a sufficient number of commonalities between the same or similar identifiers and third party identifiers thereby indicating that the same or similar identifiers actually identify the same individual (or indicates that there is a high confidence level, e.g., likelihood, that the same or similar identifiers actually identify the same individual), S424:YES, the process 400 operates to generate an output that is representative of the identity of the individual and/or an output that is representative of the confidence level that a single individual has been identified, S426. The output can be in an obfuscated or un-obfuscated (e.g., hashed or un-hashed) form.

In certain examples, the output can comprise a universally unique index to which other attributes (e.g., name, address, phone number, or e-mail address) can be added. In certain examples, the output can comprise a single identifier (e.g., a single name or single social security number, etc., and/or or a data profile of a single individual). The data profile on the single individual can include person-to-person relationship data (and demographic data if desired) from one, a plurality, or all of the sources 110 that provided the data. As noted previously, the output can, additionally or alternatively, comprise a confidence level or index that can provide an indication of how confident the identity management system 120 and process 400 are that the disparate identifiers actually identify the same individual; the confidence level can be based on the quantity of commonalities found among the person-to-person relationship data. In certain examples a user or system administrator can define specific confidence levels, e.g., one commonality in person-to-person relationship data indicates a low confidence level, two commonalities in person-to-person relationship data indicates a medium, or moderate, confidence level, and three or more commonalties in person-to-person relationship data indicates a high confidence level; other and/or additional levels can also be used.

The identity management system 120 and process 400 can end its execution at operation S426 or can, optionally, continue on to transmit or return the generated output (in obfuscated or un-obfuscated form) to one or more of the sources 110, S428.

Figure 5:
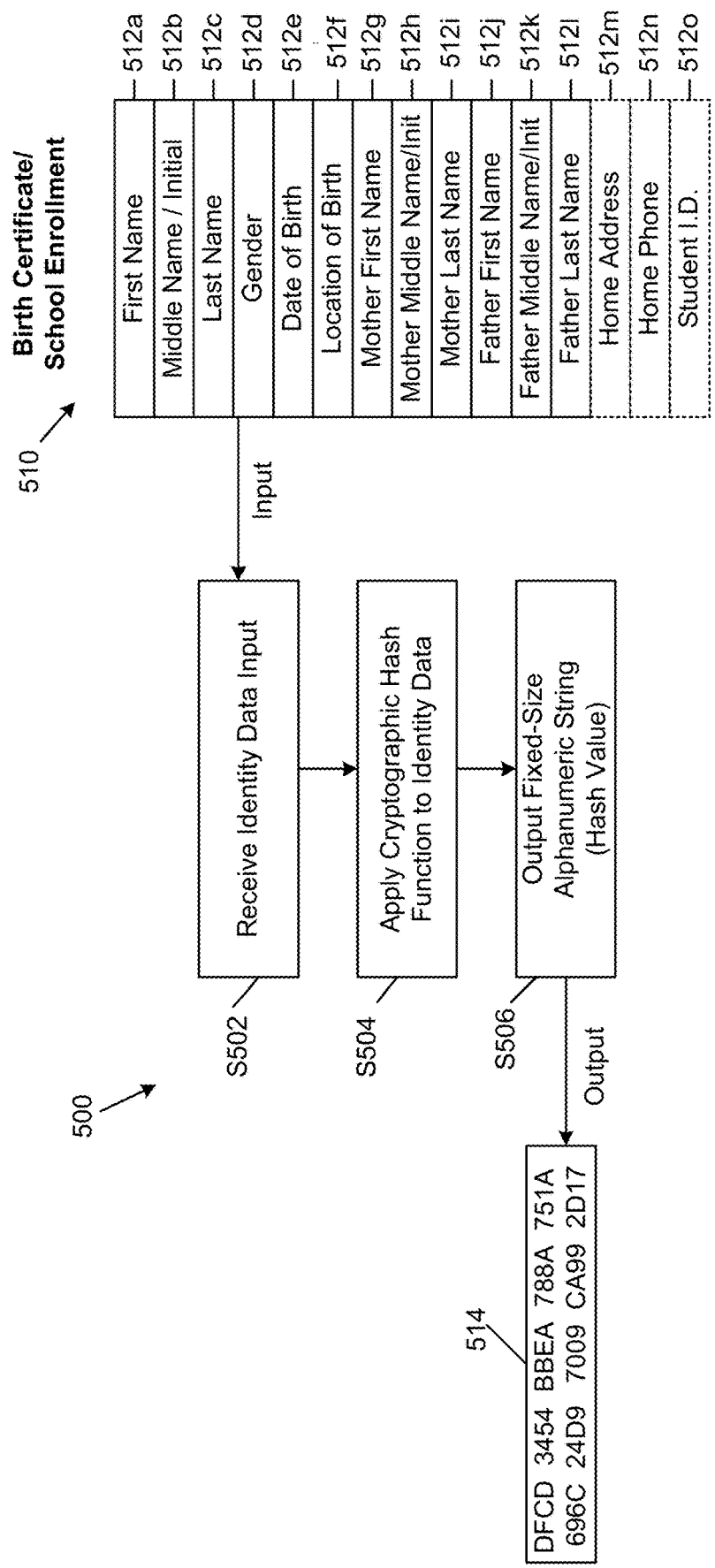
FIG. 5 is a simplified schematic illustrating the application of a cryptographic hashing function to data.

As mentioned herein, it may be desirable or necessary, to maintain the privacy of the identity data (e.g., person-to-person relationship data and/or demographic data) used by the identity management system 120 and process 400. One manner of maintaining privacy is by obfuscating the data. One manner of obfuscation comprises cryptographically hashing some or all of the inputs and/or outputs of the identity management system 120 and process 400 such that the various operations of the process 400 are performed on hashed identity data rather than ascertainable identity data. FIG. 5 provides a simplified overview of a process 500 to apply a cryptographic hash function to the identity data. First, the identity data are received at the computing device, e.g., server(s) 132, of the cryptographic data hashing system 130 (see FIG. 1), S502. The identity data can arrive as an entire record 510 for which a hash is generated, or can be broken down into smaller data fields 512*a-o* (e.g., letters, words, combination of words, sentences, etc.) at the source 110 or at the computing device 132 for hash generation. Subsequently, the cryptographic hash function is applied to the identity data, S504, wherein the hash function generates an alphanumeric bit string of a fixed size (e.g., the hash value identifier) for output, S506, such as the hash value 514.

With data hashing, the input data, e.g., the original identity data, are essentially unascertainable from the hash value. Different inputs will produce different hash values (even if the input is off from another input by only one letter or space). However, identical inputs will produce identical hash values. In the instant example, the application of the hash function to the identity data can be used to produce a hash table that enables the fast look-up of data for data correlation/commonality. A hash table is a data structure that can be used to implement an associative array, a structure that can map keys to values. A hash table uses a hash function to compute an index to any array of buckets or slots, from which the desired value can be found. Other hash structures, e.g., a hash list or a hash tree, can also be used to identify data. Other processes for obfuscating or privatizing data can also be used in place of or in conjunction with data hashing.

Figure 6:
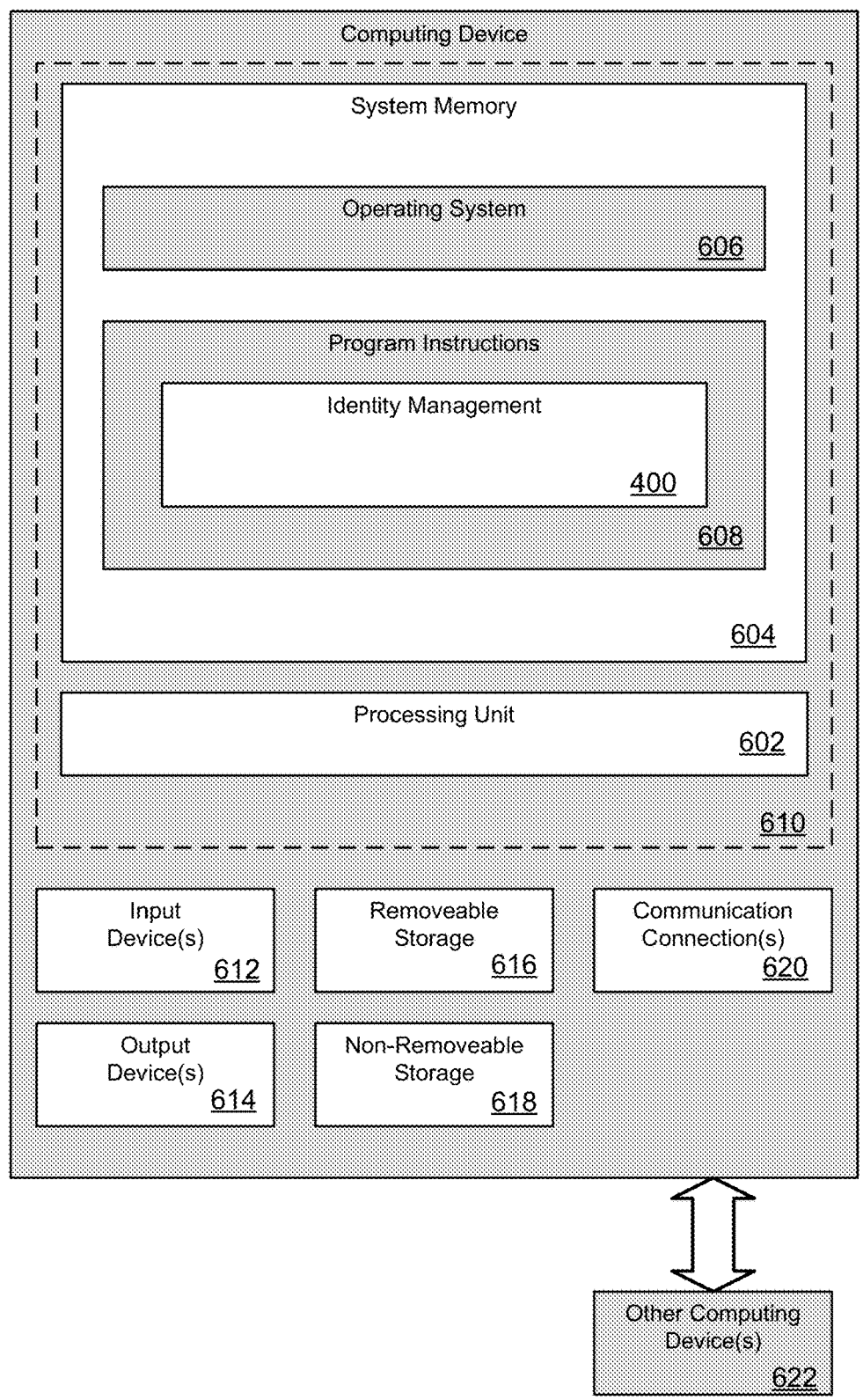
FIG. 6 is a block diagram illustrating physical components of an example computing device with which aspects of the present disclosure can be practiced.

FIG. 6 is a block diagram illustrating physical components of an example computing device with which aspects of the present disclosure may be practiced. The computing device 600 can include at least one processing unit (processor) 602 and a system memory 604. The system memory 604 may comprise, but is not limited to, volatile (e.g., random access memory (RAM)), non-volatile (e.g. read-only memory (ROM)), flash memory, or any combination thereof. System memory 604 may include operating system 606, one or more program instructions 608, and may include sufficient computer-executable instructions for the identity management process 400, which when executed, perform functionalities as described herein. Operating system 606, for example, may be suitable for controlling the operation of computing device 600. Furthermore, aspects may be practiced in conjunction with a graphics library, other operating systems, or any other application program and is not limited to any particular application or system. This basic configuration is illustrated by those components within a dashed line 610. Computing device 600 may also include one or more input device(s) 612 (keyboard, mouse, pen, touch input device, etc.) and one or more output device(s) 614 (e.g., display, speakers, a printer, etc.).

The computing device 600 may also include additional data storage devices (removable or non-removable) such as, for example, magnetic disks, optical disks, or tape. Such additional storage is illustrated by a removable storage 616 and a non-removable storage 618. Computing device 600 may also contain a communication connection 620 that may allow computing device 600 to communicate with other computing devices 622, such as over a network in a distributed computing environment, for example, an intranet or the Internet. Communication connection 620 is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit comprising discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present invention may be used in various distributed computing environments where tasks are performed by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 600 or any other computing devices 622, in combination with computing device 600, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

I claim:

1. An identity management method comprising:
    identifying at least two same or similar identifiers of individuals within data supplied by one or more data sources;
    comparing person-to-person relationship data of the at least two same or similar identifiers to determine if the at least two same or similar identifiers have a common link to a third party identifier by:
        establishing a first common link upon identifying a first third party identifier comprising a name of a relative associated with the at least two same or similar identifiers; and
        establishing a second common link upon identifying a second third party identifier comprising a name of a doctor associated with the at least two same or similar identifiers;
    when determining that the at least two same or similar identifiers have at least one common link to a corresponding third party identifier, generating an output representative of an identity of one individual having the at least one common link to the corresponding third party identifier;
    determining a first confidence level associated with the output that the at least two same or similar identifiers identify the one individual according to an established first common link associated with the first third party identifier comprising the name of the relative;
    determining a second confidence level associated with the output that the at least two same or similar identifiers identify the one individual according to an established second common link associated with the second third party identifier comprising the name of the doctor;
    determining a third confidence level associated with the output that the at least two same or similar identifiers identify the one individual according to an established first common link associated with the first third party identifier comprising the name of the relative and an established second common link associated with the second third party identifier comprising the name of the doctor, wherein the third confidence level is greater than either of the first confidence level or the second confidence level; and
    obfuscating the output.

2. The identity management method of claim 1, further comprising:
    when determining that the at least two same or similar identifiers do not have the at least one common link, generating an output indicating that the at least two same or similar identifiers may not identify the individual.

3. The identity management method of claim 1, further comprising providing a response that includes the output and one or more confidence levels responsive to an identity request from a user device.

4. The identity management method of claim 1, further comprising obfuscating the person-to-person relationship data.

5. The identity management method of claim 4, wherein obfuscating comprises cryptographically hashing.

6. The identity management method of claim 1, wherein obfuscating the output comprises cryptographically hashing.

7. The identity management system of claim 1, further comprising:
   comparing demographic data of the at least two same or similar identifiers.

8. An identity management system comprising:
   a processor comprising a processor of a computing device; and
   a memory comprising a memory of the computing device, wherein the processor is configured to execute instructions stored in the memory, wherein execution of the instructions causes the processor to:
   compare person-to-person relationship data of at least two identifiers to determine if the at least two identifiers have a common link with a third party identifier, the person-to-person relationship data obtained from one or more sources and the at least two identifiers being the same or similar, wherein to compare is to:
      establish a first common link upon identifying a first third party identifier comprising a name of a relative associated with the at least two identifiers; and
      establish a second common link upon identifying a second third party identifier comprising a name of a doctor associated with the at least two identifiers;
   when having determined that the at least two identifiers have at least one common link to a corresponding third party identifier, generate an output representative of an identity of one individual having the at least one common link with the corresponding third party identifier;
   determine a first confidence level associated with the output that the at least two identifiers identify the one individual according to an established first common link associated with the first third party identifier comprising the name of the relative;
   determine a second confidence level associated with the output that the at least two identifiers identify the one individual according to an established second common link associated with the second third party identifier comprising the name of the doctor;
   determine a third confidence level associated with the output that the at least two identifiers identify the one individual according to an established first common link associated with the first third party identifier comprising the name of the relative and an established second common link associated with the second third party identifier comprising the name of the doctor, wherein the third confidence level is greater than either of the first confidence level or the second confidence level; and
   obfuscate the output.

9. The identity management system of claim 8, wherein execution of the instructions further causes the processor to:
   when having determined that the at least two identifiers do not have at least one common link, generate an output indicating that the at least two identifiers may not identify the one individual.

10. The identity management system of claim 8, further to provide a response that includes the output and one or more confidence levels in response to an identity request from a user device.

11. The identity management system of claim 8, wherein execution of the instructions further causes the processor to:
    obfuscate the person-to-person relationship data.

12. The identity management system of claim 8, wherein execution of the instructions further causes the processor to:
    obfuscate the output according to a cryptographic hash function.

13. The identity management system of claim 11, wherein obfuscation of the person-to-person relationship data comprises application of a cryptographic hash function to the person-to-person relationship data.

14. The identity management system of claim 8, further comprising a user interface device in communication with the processor, the user interface device enabling entry of an identity request by a user of the identity management system.

15. A non-transitory computer readable medium that includes instructions which, when executed, operate to:
    receive an identity request to identify at least two same or similar identifiers of individuals within data supplied by one or more data sources;
    compare person-to-person relationship data of the at least two same or similar identifiers to determine if the at least two same or similar identifiers have a common link to a third party identifier, wherein to compare is to:
       establish a first common link upon identifying a first third party identifier comprising a name of a relative associated with the at least two same or similar identifiers; and
       establish a second common link upon identifying a second third party identifier comprising a name of a doctor associated with the at least two same or similar identifiers;
    when having determined that the at least two same or similar identifiers have at least one common link to a corresponding third party identifier, generate an output representative of an identity of one individual having the at least one common link to the corresponding third party identifier;
    determine a first confidence level associated with the output that the at least two same or similar identifiers identify the one individual according to an established first common link associated with the first third party identifier comprising the name of the relative;
    determine a second confidence level associated with the output that the at least two same or similar identifiers identify the one individual according to an established second common link associated with the second third party identifier comprising the name of the doctor;
    determine a third confidence level associated with the output that the at least two same or similar identifiers identify the one individual according to an established first common link associated with the first third party identifier comprising the name of the relative and an established second common link associated with the second third party identifier comprising the name of the doctor, wherein the third confidence level is greater than either of the first confidence level or the second confidence level; and
    obfuscate the output.

16. The non-transitory computer readable medium of claim 15, wherein the third party identifiers are identifiers of a family member, a service provider, and/or a legal representative.

17. The non-transitory computer readable medium of claim 15, when it is determined that the two or more identifiers that are the same or similar do not have one or more common links to third party identifiers, determine that two or more identifiers that are the same or similar may not comprise the one individual and generate an output representative of the determination.

18. The non-transitory computer readable medium of claim 15, wherein the output is obfuscated according to a cryptographic hash function.

19. The non-transitory computer readable medium of claim 18, wherein the person-to-person relationship data is obfuscated using cryptographic hashing.

20. The non-transitory computer readable medium of claim 19, further to provide a response that includes the output and one or more confidence levels responsive to an identity request from a user device.

* * * * *